(12) United States Patent
Tsubouchi

(10) Patent No.: US 6,175,053 B1
(45) Date of Patent: Jan. 16, 2001

(54) WOUND DRESSING MATERIAL CONTAINING SILK FIBROIN AND SERICIN AS MAIN COMPONENT AND METHOD FOR PREPARING SAME

(75) Inventor: Kozo Tsubouchi, 15-8, Matsumaedai 6-chome, Moriya-cho, Kitasouma-gun, Ibaraki 302-0102 (JP)

(73) Assignees: Japan as represented by Director General of National Institute of Sericultural and Entomological Science Ministry of Agriculture, Forrestry and Fisheries; Kozo Tsubouchi, both of Ibaraki (JP)

( * ) Notice: Under 35 U.S.C. 154(b), the term of this patent shall be extended for 0 days.

(21) Appl. No.: 09/242,528
(22) PCT Filed: Jun. 15, 1998
(86) PCT No.: PCT/JP98/02622
 § 371 Date: Feb. 17, 1999
 § 102(e) Date: Feb. 17, 1999
(87) PCT Pub. No.: WO98/57676
 PCT Pub. Date: Dec. 23, 1998

(30) Foreign Application Priority Data

Jun. 18, 1997 (JP) .................................................... 9-177705

(51) Int. Cl.$^7$ ...................................................... A61F 13/00
(52) U.S. Cl. ................................ 602/43; 602/41; 602/44; 602/45; 602/46; 602/47

(58) Field of Search .................................. 602/41, 43–47; 604/383, 358, 366, 378

(56) References Cited

U.S. PATENT DOCUMENTS

| | | | |
|---|---|---|---|
| 4,233,211 | * | 11/1980 | Ohtomo et al. . |
| 4,524,064 | * | 6/1985 | Nambu . |
| 4,818,291 | * | 4/1989 | Iwatsuki et al. . |
| 5,449,352 | * | 9/1995 | Nishino et al. . |

FOREIGN PATENT DOCUMENTS

| | | | |
|---|---|---|---|
| 2-34171 | * | 5/1990 | (JP) . |
| 2-233128 | * | 9/1990 | (JP) . |

* cited by examiner

*Primary Examiner*—Michael A. Brown
*Assistant Examiner*—Lalita M. Hamilton
(74) *Attorney, Agent, or Firm*—Flynn, Thiel, Boutell & Tanis, P.C.

(57) ABSTRACT

There is provided a novel wound dressing material which has biocompatibility and infection controllability as essential properties required for such a material, especially excellent flexibility and water absorption properties, thereby accelerating smooth regeneration of a skin defect without stripping off the regenerating skin while removing the material from the skin. A healing agent is added to the wound dressing material which comprises an amorphous film of a crystallinity below 10% and contains fibroin and sericin as a main component.

18 Claims, No Drawings

WOUND DRESSING MATERIAL CONTAINING SILK FIBROIN AND SERICIN AS MAIN COMPONENT AND METHOD FOR PREPARING SAME

TECHNICAL FIELD

This invention relates to a wound dressing material for dressing skin defect regions caused by a wound or burn and accelerating a cure of these regions and a method for preparing the same.

BACKGROUND TECHNOLOGY

In general, wound dressing materials used for healing skin defect regions are required to have the following properties and functions:

1) improved skin compatibility without irritating the skin,
2) flexibility sufficient to expand as the skin moves, and
3) infection controllability.

In order to provide these properties and functions, there have been developed wound dressing materials comprising bio-originated substances such as a pig skin, chitin and collagen or other porous substances.

When a skin defect is caused by a wound, burn, etc., the defect regions are treated by being covered with a conventional wound dressing material as a first aid and then grafting skin from buttocks or other parts to the defect region after the condition thereof is recovered to a level to be further treated.

When a conventional wound dressing material is used, however, the dressing material should be stripped off wherever the defect region is treated.

On all such occasions, new skin, which is regenerating under the dressing material is unfavorably destroyed.

Further, the flexibility of conventional dressing materials comes into question because these materials do not flexibly deform enough following the movement of the skin, which sometimes causes pain.

In the case of porous dressing materials, the infection controllability thereof is also called in question in addition to the flexibility.

As a medical material originating from a protein fiber, silk has been used for a long time as an excellent biocompatible suture.

A permeable membrane which comprises a crystalline substance containing- and water insoluble-fibroin is known as a membrane comprising a protein fiber-originated component (see, Japanese Patent Laid-Open Publication Nos. 63-246,169 and 1-118,545).

A water insoluble fibroin membrane described in Japanese Patent Laid-Open Publication No. 1-118,545 has various uses such as artificial skins, wigs, sweat clothes and the like because of excellent vapor permeability, improved transparency and mechanical strength, and desirable affinity to the human body.

On the other hand, Japanese Patent Laid-Open Publication No. 2-233,128 describes that a crystalline substance containing- and water insoluble-membrane prepared from fibroin and sericin exhibits excellent oxygen permeability, improved transparency and mechanical strength, desirable biocompatiblity and high stability to the human body, and is accordingly useful as contact lenses, artificial skins, blood bags and the like.

Furthermore, Japanese Patent Laid-Open Publication No. 56-40,156 describes that a porous membrane is prepared by blending a water soluble compound such as ethylene glycol, polyalkylene glycol and glycerine to sericin, which exhibits appropriate water absorption properties and vapor permeability required for a skin protecting material, and improved flexibility.

In these crystalline substance containing membranes which comprise water insoluble fibroin, the crystallinity thereof is necessarily at least more than 10%, and preferably more than 15% so as to keep the mechanical strength, while the water content is about 10 to 60% by weight. The crystallinity should be more than 20%, particularly in the case of the above mentioned porous membrane in which the above-mentioned water soluble compound is blended to fibroin.

Fibroin containing permeable membranes of the conventional type, in which the crystallinity is more than 10% to adequately keep the mechanical strength, may be used as artificial skins.

However, these conventional membranes exhibit insufficient flexibility and water absorption properties to use as a wound dressing material for healing a skin defect region, while in the case of porous membranes, the infection controllability is also in question, and accordingly, it is not intended in essence to use such permeable membranes themselves as a wound dressing material.

DISCLOSURE OF THE INVENTION

It is an object of the present invention to provide a novel wound dressing material which has biocompatibility and infection controllability as essential properties required for such a material, as well as excellent flexibility and water absorption properties, thereby accelerating smooth regeneration of a skin defect without stripping off the regenerating skin while removing the material from the skin, and a method for preparing the same.

The inventor has found that an amorphous film comprising fibroin as a main component is an excellent wound dressing material.

As a result of our eager investigation continued after our previous patent application (Japanese Patent Application No. 8-28,559), it has been also found that a highly flexible and water-absorbing amorphous film of a crystallinity below 10% exhibits particularly excellent properties as a wound dressing material when fibroin is combined with sericin, which has a binder-like function to fibroin.

The present invention has thus completed on the basis of the above mentioned information.

According to the present invention, there are provided a wound dressing material which comprises (a) an amorphous film of crystallinity below 10% containing fibroin and sericin as a main component, and a powder type wound dressing material which comprises (b) fibroin and sericin as a main component, and a method for preparing these wound dressing materials.

In order to further improve the healing effect to a wounded region, various healing agents or remedies may be added to these wound dressing materials as set forth in the following.

There may be added disinfectants (additives used for microorganism elimination or ablution) such as iodine, potassium iodide, povidon iodine, acrinol, hydrogen peroxide, isopropyl methylphenol, benzalkonium chloride, cetyl chloride pyridinium, chlorohexidine and the like.

There may also be added at least one or more than two kinds of cure accelerating agents (additives for accelerating a wound treatment) selected from a group consisting of, for example, allantoin, dibucaine hydrochloride, chlorophenylamine malate and the like.

Further, a vasoconstrictor such as naphazoline hydrochloride may be added.

An astringent such as zinc oxide may also be added.

Furthermore, a crust regenerating agent such as boric acid may be added.

All of these additives may be added in a selectively combined use of two or more.

The amount of the above mentioned disinfectants to be added to the wound dressing material is preferably less than 30% by weight, more preferably 0.5 to 20% by weight and most preferably 1 to 15% by weight so as not to lose the essential properties of the material. If the amount increases over 30% by weight, the wound dressing material becomes hard and fragile.

The wound dressing material of an amorphous film (a) comprises a dense and non-porous film of a crystallinity below 10% which contains 0 to 99% by weight of fibroin and 1 to 100% by weight of sericin and has a density of 1.1 to 1.4 g/cm$^3$ determined by the density-gradient tube method using toluene and tetrachlorocarbon, a thickness of 10 to 130 $\mu$m, water absorption of 100% or more after one hour-immersion in water at room temperature and a water soluble portion in an amount of 10% or more. The powder type wound dressing material (b) is obtained by milling and pulverizing the amorphous film (a).

The density is preferably 1.36 to 1.38 g/cm$^3$. The film tends to be porous because of foams when the density is less than 1.1 g/cm$^3$, while the crystallinity increases excessively when the density is more than 1.4 g/cm$^3$.

Similarly, a film of 10 $\mu$m or less in thickness is easily torn, while the crystallinity increases undesirably when the thickness is more than 130 $\mu$m.

The wound dressing material of the present invention is basically prepared from a raw material, which contains protein fiber-originated fibroin and sericin obtained from silkworms, by dissolving the raw material in an aqueous solvent in the presence of a neutral salt for dissolving the protein fiber, casting an aqueous solution of fibroin and sericin on a solid surface after demineralization thereof, followed by drying.

The raw material used to prepare the wound dressing material of the present invention includes all protein fiber materials obtained from silkworms such as house silkworms and wild silkworms, i.e., i) those materials selected from a group consisting of cocoon filaments, raw silk, silk fabrics, silk yarn (fibroin fiber) or unscoured materials thereof, ii) fibroin or sericin independently separated and prepared from cocoon filaments, raw silk, silk fabrics, and unscoured materials thereof, iii) a mixture of materials selected from a group consisting of cocoon filaments, raw silk, silk fabrics, silk yarn or unscoured materials thereof with independently separated and prepared fibroin or sericin, and iv) used products of sericin and fibroin containing fibers, powders, films and the like.

The wound dressing material of the present invention is characteristically prepared by dissolving the above mentioned materials in an aqueous solution of a neutral salt, removing insolubles from the solution by filtration or centrifugation to form a fibroin- and sericin containing aqueous solution, then demineralizing the neutral salt in the aqueous solution through dialysis to form a fibroin-sericin aqueous solution, casting the thus formed solution on a smooth solid surface, followed by drying.

Further, the wound dressing material of the present invention may be prepared through processes in which an aqueous solution of fibroin and an aqueous solution of sericin are mixed, demineralized and dried.

The wound dressing material of the present invention may also be prepared by adding fibers, powders or films which contain sericin and fibroin to a solution formed by mixing an aqueous solution of fibroin and an aqueous solution of sericin, dissolving these fibers, powders or films by adding a neutral salt, demineralizing the neutral salt in the aqueous solution through dialysis, removing the insolubles from the aqueous solution by filtration or centrifugation, then casting the aqueous solution on a smooth solid surface, followed by drying.

The above mentioned neutral salt as a dissolving agent of the raw materials such as cocoon filaments, raw silk, silk fabrics, silk yarn and the like includes, for example, calcium chloride, cupri-ethylenediamine, sodium thiocyanate, lithium thiocyanate, lithium bromide, magnesium nitrate and the like.

Alcohols such as methyl alcohol, ethyl alcohol and propyl alcohol may be added to the neutral salt with stirring at a temperature of 94° C. or less to accelerate dissolution thereof during a process for dissolving the raw material such as cocoon filaments, raw silk, silk fabrics or silk yarn in the neutral salt.

The present wound dressing material which comprises an amorphous film containing fibroin and sericin as a main component includes a wound dressing material and a powder type material in which the crystallinity is controlled in the drying process of a film forming stage to finally reduce the level below 10%, while on the contrary, in a conventional crystalline permeable membrane which comprises fibroin and sericin, the raw materials are treated in an aqueous medium of methanol 50:water 50 after the membrane formation, with the crystalization thereof being positively performed to yield a water insoluble membrane.

Accordingly, the wound dressing material of the present invention exhibits excellent biocompatibility, flexibility and infection controllability as essential properties required for such a material and, in addition, becomes more flexible through adequate absorption of the body fluid oozing out of a wounded region when the material is applied to the wound.

As a result, the pain decreases because of the lower resistance of the dressing material to the movement of the skin including the wounded region, and regenerating skin tissue can never be stripped off when the material is removed from the wounded surface for a further treatment in the healing process, because the wounded region is kept in a dry condition.

It is not necessary to change the wound dressing material until the wound is completly cured when the material contains a healing aid.

In this case, the wounded surface is tightly protected by the dressing material without any possible extrinsic infection until the wound is cured, and accordingly, the present material exhibits many excellent properties as a wound dressing material.

BEST MODE FOR CARRYING OUT THE INVENTION

Using the above mentioned starting materials, the wound dressing material of the present invention can be prepared by, for example, the following methods I to III.

I. Method for Preparing a Wound Dressing Material Starting From a Raw Material Containing Both Fibroin and Sericin In this method, a wound dressing material which comprises an amorphous film containing fibroin and sericin is prepared by dissolving a raw material in an aqueous solution of a neutral salt, demineralizing the neutral salt in the aqueous solution through dialysis to form a fibroin-sericin containing aqueous solution, removing insolubles from the aqueous solution by filtration or centrifugation, and then casting the aqueous solution on a smooth solid surface, followed by drying, the raw material being selected from a group consisting of cocoon filaments, raw silk, silk fabrics, silk yarn or unscoured materials thereof which comprise fibroin and sericin originated from protein fibers as a silkworm product and are obtained from house cocoons or wild cocoons, or being prepared by mixing the above mentioned raw material and fibroin or serisin originated from protein fibers as a silkworm product.

The above mentioned fibroin or sericin originated from protein fibers as a product of silkworms is defined as in the following.

Fibroin is a material obtained by boiling cocoon filaments, raw silk, silk fabrics, silk yarn, etc. in an aqueous alkali such as sodium hydrogencarbonate or sodium hydroxide and washing with water, while sericin is a material obtained by boiling unscoured or completely scoured materials of cocoon filaments, raw silk, silk fabrics, silk yarn, etc. in water or an aqueous alkali and drying and solidifying the boiling solution.

As the raw material of this method, there may be used a solid state mixture of fibroin and sericin with cocoon filaments, raw filaments, silk fabrics, silk yarn or unscoured materials thereof.

This process consists of the following processes (a) to (e).

(a) A dissolving process in which the above mentioned raw material is dissolved in an aqueous solution of a neutral salt as a dissolving agent such as potassium chloride, cupriethylenediamine, sodium thiocyanate, lithium thiocyanate, lithium bromide and magnesium nitrate.

When alcohol such as methyl alcohol, ethyl alcohol and propyl alcohol is used as the above mentioned aqueous solution, it is possible to increase the solubility of the cocoon filaments, raw silk, silk fabrics, etc. and to decrease the dissolving temperature thereof. The dissolving process is conducted at the dissolving temperature of 94° C. or less, and desirably about 85° C.

(b) A removing process in which insolubles such as undissolved cocoon filaments, raw silk, silk fabrics, silk yarn or molted residues are removed from the dissolution liquid obtained in the process (a), if necessary, by filtration or centrifugation to yield a mixed fibroin-sericin dissolution liquid.

(c) A dialysis process in which the neutral salt and lower molecular materials having a molecular weight of about 5,000 or less, such as an alcohol, in the dissolution liquid obtained in the process b) are removed by means of a dialysis membrane or dialysis equipment to yield a mixed fibroin-sericin aqueous solution.

(d) A purification process in which precipitated materials in the mixed fibroin-sericin aqueous solution is removed by filtration, centrifugation or any other means to purify thereof.

(e) A casting process in which the mixed aqueous solution of purified fibroin-sericin is cast on a horizontal surface or put on a roll surface to form a thin layer, which is then dehydrated and dried by various conventional means to form a film.

As a dehydration and drying means, there may be used heat drying at a temperature of 100° C. or less, drying at room temperature by controlling the humidity, supercooling drying at a temperature of −4 to −5° C., vacuum drying and the like.

It is necessary in the drying process to control the drying condition so that the crystallinity of the finally obtained film is not more than 10%.

In particular, it is important that the drying process should be completed in a short period of time when the water content in the thin layer reaches 100% or less after the water content is gradually reduced by hydration.

A crystalline diffraction is slightly observed in the vicinity of about 4 A in addition to an amorphous halo diffraction, when the period of drying is extended. If the period is further extended, crystallization is stimulated to increase the crystallinity up to 10% or more in the end.

According to these processes, an amorphous film of crystallinity below 10% and containing mixed fibroin and sericin is prepared, which is used as a wound dressing material.

II. Method for Preparing a Wound Dressing Material in Which Fibroin and Sericin are Prepared Independently, Followed by Forming a Film From a Mixed Solution Therefrom In this method, independently prepared fibroin and sericin are dissolved in an aqueous medium separately and then mixed together to form a mixed solution, which is used for film formation. Such a mixing process may be conducted any point of time when the mixture is in a state of solution.

For example, the mixing process may be conducted at a point of time when fibroin and sericin are added with a neutral salt as a dissolving agent.

The process may also be conducted at a point of time when fibroin and sericin are respectively in a state of aqueous solution from which the neutral salt has been removed.

Further, the process may be conducted at a point of time when one of fibroin or sericin is added with the dissolving agent and the other fibroin or sericin is in a state of aqueous solution from which the dissolving agent has been removed through dialysis.

This method comprises four processes (A) to (D) as in the following.

(A) Process for preparing a fibroin aqueous solution.

(f) Protein fibers such as cocoon filaments, raw silk, silk fabrics, etc. as a product of house silkworms or wild silkworms are scoured to remove sericin so as to yield a fibroin inner layer.

In general, silk yarn comprises fibroin in an amount of 97% or more, wax as the other major component, and a slight amount of tannin, sericin, dust and the like.

The fibroin may either be in the state of a powder or a film.

(g) The thus scoured fibroin is dissolved in an aqueous solution of a neutral salt.

(h) The aqueous solution of fibroin is subjected to dialysis to remove the neutral salt, followed by further removal of precipitates so as to yield an intended aqueous fibroin solution.

(B) Process for preparing a sericin aqueous solution.

(i) In order to recover sericin in a liquid state from an outer layer of protein fibers where sericin adheres in a solid state, an aqueous solution of sericin and an acid or alkali-containing aqueous solution of sericin is yielded from protein fibers of cocoon fibers, raw silk, silk fabrics, etc. as a product of house silkworms or wild silkworms, using water and an aqueous solution of a sericin-dissolving agent such as an acid or alkali, respectively.

(j) The aqueous solution of sericin is subjected to dialysis to remove lower molecular materials such as an acid or alkali, followed by further removal of precipitates so as to yield an intended aqueous sericin solution.

After water is removed from the aqueous sericin solution, the product comprises sericin in an amount of 90% or more, wax as the other major component, and a slight amount of tannin, dust and the like.

(C) Process for preparing a mixed fibroin-sericin solution.

(k) Fibroin prepared by the process (A) and sericin prepared by the process (B) may be mixed at any point of time.

If the mixed solution contains the dissolving agent for fibroin or sericin, such an agent is removed through dialysis to yield the mixed fibroin-sericin aqueous solution.

(D) Process for preparing a mixed fibroin-sericin film.

(l) A film type wound dressing material is prepared by casting the mixed fibroin-sericin aqueous solution to form a thin layer, removing water and drying.

In the above mentioned processes, removal of undissolved materials such as wax, tannin, dust, etc. may be carried out at any point of time during the preparing processes of the wound dressing material, if necessary, until the mixed fibroin-sericin aqueous solution is cast as a thin layer, although the undissolved materials are necessarily removed when fibroin and sericin are in a state of a mixed aqueous solution.

As a method for adjusting the fibroin-sericin content, it is also possible to add fibroin or sericin in a form of fiber, powder or film in the process for preparing the aqueous fibroin or sericin solution so as to yield the amorphous film of mixed fibroin and sericin.

Such a form of fibroin or sericin to be added to each solution thereof, respectively, may be prepared in a variety of manners in which the aqueous fibroin or sericin solution as a product of the above mentioned process (A) or (B) is subjected to freeze-drying, drying on a horizontal plate, spray-drying and the like, followed by mechanical grinding.

Further, according to the present invention, it is possible to prepare a wound dressing material which is applicable to various skin regions by changing the ratio of fibroin to sericin during the preparing process so that properties, especially water absorption properties can be altered.

In the preparing process of the present wound dressing material, it is preferable to add a variety of remedies such as the above mentioned disinfectants, treatment accelerating agents, vasoconstrictors, astringents, crust regenerating agents and the like so as to increase the treating effect of the material.

For this reason, the wound dressing material can be positively applied to treatments of various kinds of skin defects.

When the remedies are added to the wound dressing material, they may be mixed in the material during the processes (I and II) for preparing the fibroin-sericin mixed film.

More specifically, the remedies may be added to the wound dressing material during any process of the above mentioned (a) to (l), but preferably at a point of time when fibroin and sericin are in a state of a mixed aqueous solution.

Even when the remedies are added to the wound dressing material, it is important to keep the crystallinity of the fibroin-sericin portion below 10%.

In order to alter properties of the wound dressing material such as water absorption properties, stretchability and strength, there may be added thereto an adequate amount of a synthetic high polymer such as polyamino acid, or a wide range of materials from natural origins such as wool, chitin, chitosan, cellulose and the like in the form of fiber, powder or liquid.

These materials are compatible to the wound dressing material because of their natural originality.

III. Method for Preparing a Powder Type Dressing Material for a Skin Defect

The film prepared as mentioned above may be mechanically ground to form a powder type dressing material for a skin defect.

The grain size of the powder is about 2 to 200 $\mu$m, and preferably 5 to 20 $\mu$m. The powder tends to be dispersed in the grain size less than 2 $\mu$m, while it is difficult to control the crystallinity below 10% in the grain size over 200 $\mu$m, because the thickness of the film should be thickened.

For a desirable grinding process thereof, the water content of the film is about 20% or less, and preferably 8% or less.

Apparent specific gravity of the powder changes depending on the preparing process employed. For example, the apparent specific gravity of a powder prepared by grinding the film is higher than that of a powder prepared by a freeze-drying process because of the porosity thereof.

As has been described above, the wound dressing material of the present invention exhibits considerably excellent biocompatibility, flexibility and infection controllability, which are required as essential properties of such a material.

Further, the wound dressing material becomes more flexible due to an adequate absorption of body liquid oozing from a wounded region while applying the material thereto, so that the resistance of the material to movement of the skin including the wounded region is reduced, thereby the pain being decreased.

As the wounded region is kept in a dry condition by means of the wound dressing material, regenerating skin tissue can never be stripped off when the material is removed from the wounded surface during a further treatment in the healing process.

Particularly, when the wound dressing material contains having aides, it is not necessary to change the material until the wound is completely cured, so that the wounded region is tightly protected by the material without possible extrinsic infection up to the end.

Accordingly, the material of the present invention exhibits considerably excellent properties to be required as a wound dressing material.

EXAMPLE 1

This example describes an alteration in properties of a wound dressing material depending on a fibroin-sericin ratio.

A series of wound dressing materials of different fibroin-sericin ratios were prepared from raw silk as a starting material by changing the amount of sericin to be removed from the raw silk.

Raw silk comprises fibroin and sericin, while sericin content is different depending on the specific species of silkworms. In general, however, the sericin content is about 23%±2% of the raw silk used.

After the raw silk is washed in hot water for several minutes, a removal ratio of serin from the raw silk is changed by controlling a boiling period of time thereof in 0.1% aqueous sodium carbonate.

A decrease in the sericin content in raw silk was 22.3% when the raw silk was washed in hot water, followed by twice repeated boiling in 0.1% aqueous sodium carbonate for 60 minutes. The thus obtained level of 22.3% was regarded as a sericin content of the raw silk used herein, and the sericin content of each starting material was calculated on the basis of this level.

When calcium chloride is dissolved in an aqueous medium of ethyl alcohol and water to yield a dissolving solution of calcium chloride:ethyl alcohol:water=1:2:8 (molar ratio), the temperature of the solution increases up to about 85° C. The raw silk is then supplied in the solution with stirring to dissolve the silk.

It takes less than several hours to dissolve 50 g. of starting material in 1000 g. of the dissolving solution. When a starting material of smaller fines is used or the material is cut down previously to a certain length, the dissolving time can be reduced. It is also possible to further shorten the dissolving time by forcibly heating by means of a heater, etc. so that the solution is kept at a temperature less than 94° C. A temperature more than 95° C. is available if the dissolving time is in the range of several ten minutes.

The dissolving solution is introduced in a dialysis membrane bag, which is then kept in pure water to remove lower molecular materials such as calcium chloride and ethyl alcohol from a fibroin-sericin dissolving solution in water.

This dialysis is conducted while replacing the pure water at intervals of several hours.

A mixed fibroin-sericin aqueous solution in which most of the lower molecular materials are completely removed is obtained by repeating the dialysis about 10 to 20 times or continuously supplying the pure water around the dialysis bag.

While an increase in fibroin-sericin concentration in the aqueous solution to 1 to 2% stimulates the precipitation therein, precipitated or undissolved materials should be removed by filtration or centrifugation to yield an aqueous solution in which fibroin and sericin are completely dissolved.

An average molecular weight of the thus prepared fibroin and sericin is more than 50,000, respectively.

At this point of time, a variety of additives are blended in the wound dressing material to improve the properties thereof.

The aqueous solution was cast on a horizontal acrylic resin plate in a humidity-controlled room and dried while blowing under a relative humidity condition of 60% RH±20% RH at room temperature to yield amorphous films A-1 to A-4.

It is possible to change the crystallinity by adequately selecting a drying speed.

It is also possible to change the film thickness by adequately selecting the concentration of the mixed aqueous solution after dialysis.

Other than the acrylic resin, there may be used plastics such as polyethylene, urethane resin, vinyl chloride resin, polyester, polypropylene, polyamide, etc., glass, metals and the like as the horizontal plate, although polyethylene is preferable because of the improved release characteristics thereof.

As a comparative example, there was prepared a conventional film (B) corresponding to an oxygen permeable membrane described in Japanese Patent Laid-Open Publication No. 2-233,128, in which the membrane was subjected to a further treatment in a 50% methyl alcohol aqueous solution for 30 to 60 minutes after the membrane was formed, followed by drying.

After these films were dipped in water at room temperature for an hour, the water absorption {weight of absorbed water/weight of dried film×100 (%)}, weight loss percentage of the film (dissolved weight in water) to the initial weight (weight loss %), initial modulus (Young' modulus) of stretched film in water, and rupture strength and stretch thereof were determined.

The crystallinity was determined from an area of X-ray (Cuκα-ray) interference strength curve of each film at a reflection angle of 2θ=5 to 40° as in the following.

(1) The X-ray interference strength is defined as the sum of the strength of a crystalline portion and an amorphous portion.

(2) An interference strength curve of the crystalline portion in the film is defined as the difference between both interference strength curves of the film and the amorphous one.

(3) Interference strength curves of each film to be determined are defined as the curves of an amorphous film when the film only exhibits amorphous halos in the X-ray diffraction image and the water solubility thereof is 100%.

(4) The crystallinity is calculated from the following equation:

(area of crystalline interference strength curve)/(sum of areas of crystalline and amorphous interference strength curves)×100 (%)

The physical properties thus obtained are shown in the following Table 1.

TABLE 1

| | Sericin Content (%) | Thickness (μm) | Water Absorption (%) | Weight Loss (%) | Young's Modulus (g/mm²) | Rupture Strength (g/mm²) | Rupture Stretch (%) | Crystallinity (%) | Density (g/cm³) |
|---|---|---|---|---|---|---|---|---|---|
| A-1 | 1.7 | 40 | ∞ | 100 | — | — | — | 0 | 1.361 |
| A-2 | 12.2 | 40 | 906 | 68 | — | — | — | 1 | 1.363 |
| A-3 | 22.3 | 50 | 603 | 58 | 140 | 55 | 238 | 4 | 1.366 |
| A-4 | 22.3 | 80 | 195 | 17 | 450 | 197 | 251 | 9 | 1.368 |
| B | 22.3 | 50 | 49 | 2 | 8,900 | 1,050 | 382 | 27 | 1.371 |

The density of these films A-1 to A-4 and film B (40 μm or 50 μm in thickness) was in the range of 1.1 to 1.4 g/cm³.

Table 1 shows clearly that films A-1 to A4 of the present invention exhibit considerably high water absorption and extremely low Young's modulus, which demonstrates the very high flexibility of these films in a water absorbed state compared with Film B.

Because of the forcible crystallization by an alcohol, film B exhibits a water absorption of about 50% or less an extremely low weight loss in water and hardly dissolves in water.

When film B was dried in the membrane forming process for several hours or longer after the water absorption was reduced to 100% or less, plural crystalline diffraction rings were confirmed from an X-ray diffraction observation as a clear evidence of crystallization.

Even when film B was not forcibly crystallized by an alcohol after drying, the film was undesirably hard and less flexible because of the lower water absorption of about 80% or less and lower weight loss in water of 7% or less. Accordingly, film B was not useful as a wound dressing material.

EXAMPLE 2

In a method for preparing a wound dressing material of the present invention, the fibroin-sericin ratio is changed widely to yield a variety of films as will be described in the following.

Raw silk was boiled in a 0.1% aqueous sodium carbonate for an hour, washed with water and dried to yield fibroin. On the other hand, raw silk was boiled in boiling water at 98 to 100° C. for 6 hours with stirring, extracted and dried to yield sericin.

The thus yielded fibroin and sericin were mixed in various ratios and dissolved in a calcium-ethyl alcohol-water solution to prepare films A-5 to A-11 in a similar manner as described in Example 1.

The density of these films (50 μm in thickness) was in the range of 1.1 to 1.4 g./cm³. The physical propertiers of these films are shown in the following Table 2.

thereby gradually increasing the crystalline portion and reducing the water absorption.

Even when the sericin content is 100%, however, the film exhibits a water absorption of 244% due to the higher water absorption of the amorphous portion. Accordingly, it is confirmed that this film also functions as a wound dressing material.

In order to examine functions of the film which would satisfy requirements as a wound dressing material, the film was applied to a corium-flayed mouse. As a result of progress observations, it was confirmed that the film effectively inhibited edematization and functioned as a wound dressing material.

The reason why is that the film absorbs enough body fluid from a wounded region to form a more flexible membrane because of the higher water absorption properties thereof. The thus formed flexible membrane adheres to the wounded region tightly, which prevents excessive flow out of body fluid or body protein, while, at the same time, smooth regeneration of the skin is accelerated, because the film deforms flexibly as the skin moves without stimulating the wounded region and skin cell-proliferating substances in the body fluid or body protein are kept on the wounded surface.

EXAMPLE 3

Using mice, further examinations were conducted.

Effects of wound dressing materials to a mouse will be examined in detail in this example.

Films A-1, A-3, A-6, A-9 and A-11 described in Examples 1 and 2 were used as a wound dressing material.

Further, film B prepared by a conventional process and films A-12 and A-13 prepared by a similar film forming process as described in Examples 1 and 2 were used in a comparative example.

The crystallinity of films A-12 and A-13 was increased by slowing down the drying speed.

TABLE 2

|   | Sericin Content (%) | Thickness (μm) | Water Absorption (%) | Weight Loss (%) | Young's Modulus (g/mm²) | Rupture Strength (g/mm²) | Rupture Stretch (%) | Crystallinity (%) | Density (g/cm³) |
|---|---|---|---|---|---|---|---|---|---|
| A-5 | 4.3 | 50 | ∞ | 100 | — | — | — | 0 | 1.362 |
| A-6 | 25.0 | 50 | 550 | 53 | 160 | 76 | 221 | 5 | 1.369 |
| A-7 | 41.7 | 50 | 378 | 41 | 85 | 22 | 183 | 7 | 1.371 |
| A-8 | 58.3 | 50 | 302 | 35 | 37 | 15 | 12 | 7 | 1.372 |
| A-9 | 71.2 | 50 | 288 | 31 | 10 | 7 | 5 | 8 | 1.377 |
| A-10 | 86.3 | 50 | 265 | 28 | — | — | — | 8 | 1.378 |
| A-11 | 100.0 | 50 | 244 | 24 | — | — | — | 9 | 1.382 |

Tables 1 and 2 clearly show that the greater the sericin content in the film, the longer the drying time is extended, Physical properties of these films are shown in the following Table 3.

TABLE 3

|   | Sericin Content (%) | Thickness (μm) | Water Absorption (%) | Weight Loss (%) | Young's Modulus (g/mm²) | Rupture Strength (g/mm²) | Rupture Stretch (%) | Crystallinity (%) | Density (g/cm³) |
|---|---|---|---|---|---|---|---|---|---|
| A-12 | 2.1 | 50 | 65 | 5 | 1,570 | 3.71 | 285 | 12 | 1.370 |
| A-13 | 18.5 | 50 | 56 | 7 | 2,380 | 4.35 | 303 | 13 | 1.372 |

A mouse was shaved and flayed to a corium to form a wounded region of about 1 cm², where was disinfected with a 7%-povidone-iodine solution and treated by applying a dressing material thereto.

The tissue of the wounded region was visually observed in connection within days after the mouse was wounded.

The result is shown in the following Table 4.

TABLE 4

| Days after wounded | Condition of Tissue | Wound Dressing Material | | | | | | | |
|---|---|---|---|---|---|---|---|---|---|
| | | A-1 | A-3 | A-6 | A-9 | A-11 | A-12 | A-13 | B |
| 7 days | Amount of Fluid on a Inflamed Region | -- | -- | -- | - | - | + | + | ++ |
| | Regeneration of Cuticle | + | + | + | - | - | -- | -- | -- |
| 14 days | Amount of Fluid on a Inflamed Region | -- | -- | -- | -- | -- | + | + | + |
| | Regeneration of Cuticle | ++ | ++ | ++ | + | + | - | -- | -- |
| 21 days | Amount of Fluid on a Inflamed Region | -- | -- | -- | -- | -- | -- | -- | -- |
| | Regeneration of Cuticle | +++ | +++ | +++ | ++ | ++ | + | + | + |

-- : no, - : scarce, + : some, ++ : medium, +++ : remarkable

In table 4, a symbol "- -" (no) appeared in an item "amount of fluid on an inflamed region" means a desirably cured condition, while a symbol "+++" (excellent) appeared in an item "regeneration cuticle" (remarkable) means a remarkably cured condition.

It was confirmed that wound dressing materials A-1 to A-11 prepared according to the present invention adhered tightly to the wounded region, adequately absorbing the fluid oozing from the wounded region, release moisture and stimulate the skin tissues to regenerate.

On the contrary, comparative films B, A-12 and A-13 absorbed the oozed fluid insufficiently so that the wound was simply in a condition of autotherapy.

EXAMPLE 4

Using mice, the effects of wound dressing materials containing a wound healing agent (disinfectant) were examined in detail.

Films AP-1, AP-2 and AP-3 were prepared in a similar manner as described in Examples 1 and 2 except that 10% by weight of a 7% povidone-iodine solution was added to each of film forming aqueous solution. Finally, each film contained 13% by weight (dry weight) of povidone-iodine.

The physical properties are shown in the following Table 5.

In an animal test, a mouse was shaved and flayed to a corium to form a wounded region of about 1 cm², where was treated by applying dressing materials AP-1, AP-2 and AP-3.

The tissues of the wounded region were visually observed in connection within days after the mouse was wounded.

The result is shown in the following Table 6.

TABLE 6

| Days after wounded | Condition of Tissue | Wound Dressing Material | | |
|---|---|---|---|---|
| | | AP-1 | AP-2 | AP-3 |
| 7 days | Amount of Fluid on a Inflamed Region | -- | -- | - |
| | Regeneration of Cuticle | + | + | - |
| 14 days | Amount of Fluid on a Inflamed Region | -- | -- | -- |
| | Regeneration of Cuticle | ++ | ++ | + |
| 21 days | Amount of Fluid on a Inflamed Region | -- | -- | -- |
| | Regeneration of Cuticle | +++ | +++ | ++ |

--: no, -: scarce, +: some, ++: medium, +++: remarkable

These wound dressing materials showed a healing effect similarly as in the case of Example 3 when the films were applied without treating the wounded region with an rid after the skin was flayed in a similar manner as used in Example 3, because a povidon-iodine solution had been mixed therein.

TABLE 5

| Wound Dressing Material | Sericin Content (%) | Thickness (μm) | Water Absorption (%) | Weight Loss (%) | Young's Modulus (g/mm²) | Rupture Strength (g/mm²) | Rupture Stretch (%) | Crystallinity (%) | Density (g/cm³) |
|---|---|---|---|---|---|---|---|---|---|
| AP-1 | 1.7 | 40 | ∞ | 100 | — | — | — | 1 | 1.362 |
| AP-2 | 12.0 | 40 | 820 | 61 | — | — | — | 2 | 1.364 |
| AP-3 | 21.9 | 50 | 550 | 55 | 150 | 60 | 210 | 5 | 1.367 |

EXAMPLE 5

Powder type wound dressing materials were prepared by pulverizing a series of films described in Examples 1 to 4 to form a powder having a grain size of about 10 μm in a similar manner as described above.

The result obtained in this example was practically same as that of the film type wound dressing materials.

In the case of the powder type wound dressing materials, however, it was possible to partly control the dosage thereof to the wound so that the material can be applied depending on, for example, the wound depth. Such an easiness is peculiar to the powder type, which is quite different from the film type.

INDUSTRIAL APPLICABILITY

The present invention is used for curing the skin when burned, activating and protecting the skin and is expected to have a remarkable effect when applied to cosmetics, underwears and socks that contact the skin.

What is claimed is:

1. A wound dressing material which comprises an amorphous film of crystallinity below 10% containing fibroin and sericin as a main component.

2. The wound dressing material claimed in claim 1, additionally comprising a healing agent as a main component.

3. The wound dressing material claimed in claim 2 in which a disinfectant selected from the group consisting of iodine, potassium iodine, povidon iodine, acrinol, hydrogen peroxide, isopropyl methylphenol, benzalkonium chloride, cetyl chloride pyridinium, and chlorohexidine is used as a healing agent.

4. A wound dressing material which comprises a dense and non-porous film of crystallinity below 10%, the film containing 0 to 99% by weight of fibroin and 1 to 100% by weight of sericin and having density of 1.1 to 1.4 g/cm$^3$, thickness of 10 to 130 μm, water absorption of 100% or more after one hour-immersion in water at room temperature and a water soluble portion in an amount of 10% or more.

5. A method for preparing a wound dressing material comprising an amorphous film of crystallinity below 10% and containing fibroin and sericin as a main component which comprises dissolving a raw material selected from the group consisting of cocoonfilaments, raw silk, silk fabrics, silk yarn or unscoured materials thereof, or obtained by mixing independently separated and prepared fibroin and sericin to said raw material in an aqueous solution of a neutral salt, demineralizing the neutral salt in the aqueous solution through dialysis to form a fibroin-sericin containing aqueous solution, removing insolubles from the aqueous solution by filtration or centrifugation, and then casting the aqueous solution on a smooth solid surface, followed by drying.

6. A method for preparing a wound dressing material claimed in claim 5 in which a neutral salt such as calcium chloride, cupri-ethylenediamine, sodium thiocyanate, lithium thiocyanate, lithium bromide and magnesium nitrate is used as a dissolving agent of the raw materials such as cocoon filaments, raw silk, silk fabrics and silk yarn.

7. A wound dressing material claimed in claim 5 in which alcohol such as methyl alcohol, ethyl alcohol and propyl alcohol is added to and dissolved in a neutral salt during a process for dissolving cocoon filaments, raw silk, silk fabrics and the like in a neutral salt solution.

8. A method for preparing a wound dressing material comprising an amorphous film of crystallinity below 10% and containing fibroin and sericin as a main component which comprises mixing an aqueous fibroin solution and an aqueous sericin solution, demineralizing and drying.

9. A method for preparing a wound dressing material comprising an amorphous film of crystallinity below 10% and containing fibroin and sericin as a main component which comprises adding fibers, powders or films which contain sericin and fibroin to a solution formed by mixing an aqueous solution of fibroin and an aqueous solution of sericin, dissolving these fibers, powders or films by adding a neutral salt, demineralizing the neutral salt in the aqueous solution through dialysis to form an aqueous solution containing fibroin and sericin, removing insolubles from the aqueous solution, then casting the aqueous solution on a smooth solid surface, followed by drying.

10. A method for preparing a wound dressing material comprising an amorphous film of crystallinity below 10% and containing fibroin and sericin as a main component which comprises dissolving fibroin and sericin obtained by independent separation and formed from a raw material selected from a group consisting of cocoon filaments, raw silk, silk fabrics or unscoured materials thereof in the presence of a neutral salt, demineralizing, casting an aqueous solution containing fibroin and sericin on a smooth solid surface, followed by drying.

11. A powder type wound dressing material which comprises fibroin and sericin as a main component.

12. A powder type wound dressing material claimed in claim 11 in which a healing agent is added to a powder type wound dressing material comprising fibroin and sericin as a main component.

13. A powder type wound dressing material claimed in claim 12 in which a disinfectant selected from the group consisting of iodine, potassium iodide, povidon iodine, acrinol, hydrogen peroxide, isopropyl methylphenol, benzalkonium chloride, cetyl chloride pyridinium, and chlorohexidine is used as a healing agent.

14. The powder type wound dressing material claimed in claim 11 which comprises 0 to 99% by weight of fibroin and 1 to 100% by weight of sericin.

15. A method for preparing a powder type wound dressing material containing fibroin and sericin as a main component which comprises dissolving a raw material selected from the group consisting of cocoonfilaments, raw silk, silk fabrics silk yarn or unscoured materials thereof containing protein fiber-originated fibroin and sericin as a silkworm product, or obtained by mixing independently separated and prepared fibroin and sericin to said raw material in an aqueous solution of a neutral salt, demineralizing the neutral salt in the aqueous solution through dialysis to form a fibroin-sericin containing aqueous solution, removing insolubles from the aqueous solution by filtration or centrifugation, and then casting the aqueous solution on a smooth solid surface, drying and pulverizing the thus obtained amorphous film of crystallinity below 10% which contains fibroin and sericin as a main component.

16. A method for preparing a powder type wound dressing material containing fibroin and sericin as a main component which comprises dissolving fibroin or sericin, which is separated and obtained from a raw material selected from a group consisting of cocoonfilaments, raw silk, silk fabrics silk yarn or unscoured materials thereof containing protein fiber-originated fibroin and sericin as a silkworm product, in an aqueous medium in the presence of a neutral salt, demineralizing the neutral salt in the aqueous solution through dialysis to form a fibroin-sericin containing aqueous solution, removing insolubles from the aqueous solution by filtration or centrifugation, and then casting the aqueous solution on a smooth solid surface, drying and pulverizing the thus obtained amorphous film of crystallinity below 10% which contains fibroin and sericin as a main component.

17. A method for preparing a powder type wound dressing material containing fibroin and sericin as a main component which comprises mixing fibroin and sericin in a state of solution, demineralizing, drying and pulverizing the thus obtained amorphous film of crystallinity below 10% which contains fibroin and sericin as a main component.

18. A method for preparing a powder type wound dressing material containing fibroin and sericin as a main component which comprises adding fibers, powder and film of sericin or fibroin to fibroin or sericin in a state of solution, demineralizing, drying and pulverizing the thus obtained amorphous film of crystallinity below 10% which contains fibroin and sericin as a main component.

* * * * *